(12) United States Patent
Lundkvist et al.

(10) Patent No.: US 6,625,486 B2
(45) Date of Patent: Sep. 23, 2003

(54) METHOD AND APPARATUS FOR INTRACELLULAR DELIVERY OF AN AGENT

(75) Inventors: Andre-Jean S. Lundkvist, Santa Clara, CA (US); Elisa J. Aldridge, Stanford, CA (US); Vinayak D. Bhat, Sunnyvale, CA (US); Renee C. Slater, Santa Clara, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/833,149

(22) Filed: Apr. 11, 2001

(65) Prior Publication Data

US 2002/0151866 A1 Oct. 17, 2002

(51) Int. Cl.⁷ .................................................. A61N 1/30
(52) U.S. Cl. ............................................................ 604/21
(58) Field of Search ............................... 604/19, 20, 21

(56) References Cited

U.S. PATENT DOCUMENTS

| | | | | |
|---|---|---|---|---|
| 4,411,648 A | * | 10/1983 | Davis et al. ................. 604/21 |
| 5,041,107 A | * | 8/1991 | Heil, Jr. ................... 604/891.1 |
| 5,336,205 A | | 8/1994 | Zenzen et al. .............. 604/280 |
| 5,413,581 A | | 5/1995 | Goy ............................. 606/194 |
| 5,415,636 A | | 5/1995 | Forman ........................ 604/101 |
| 5,439,440 A | | 8/1995 | Hofmann ....................... 604/20 |
| 5,628,728 A | * | 5/1997 | Tachibana et al. ............ 604/19 |
| 5,693,029 A | | 12/1997 | Leonhardt .................... 604/264 |
| 5,702,359 A | | 12/1997 | Hofmann et al. .............. 604/20 |
| 5,797,870 A | | 8/1998 | March et al. .................. 604/49 |
| 5,921,982 A | | 7/1999 | Lesh et al. .................... 606/41 |
| 5,944,710 A | * | 8/1999 | Dev et al. ...................... 604/21 |
| 6,068,650 A | | 5/2000 | Hofmann et al. .............. 607/2 |
| 6,120,520 A | | 9/2000 | Saadat et al. ................ 606/170 |
| 6,165,164 A | | 12/2000 | Hill et al. .................... 604/523 |
| 6,216,033 B1 | * | 4/2001 | Southam et al. .............. 604/20 |

FOREIGN PATENT DOCUMENTS

WO      WO 00/10552      3/2000      .......... A61K/31/00

* cited by examiner

Primary Examiner—Edward K. Look
Assistant Examiner—John K. Fristoe, Jr.
(74) Attorney, Agent, or Firm—Squire, Sanders & Dempsey, L.L.P.

(57) ABSTRACT

A method and an apparatus for electropermeabilization-mediated intracellular delivery of an agent are provided.

25 Claims, 2 Drawing Sheets

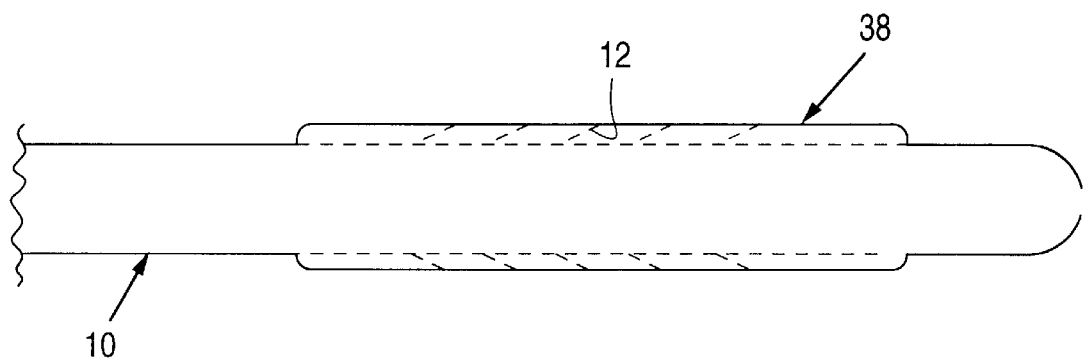
FIG. 2C
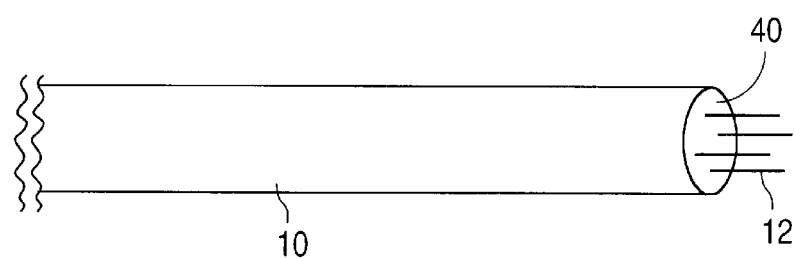
FIG. 3
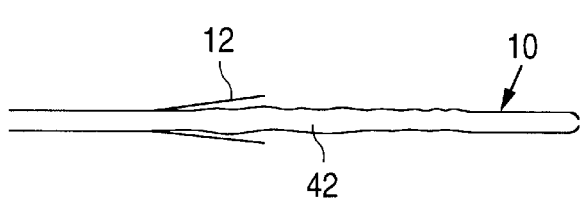 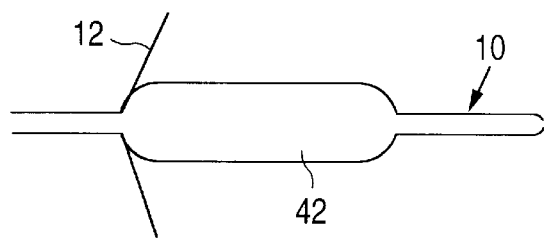
FIG. 4A      FIG. 4B

METHOD AND APPARATUS FOR INTRACELLULAR DELIVERY OF AN AGENT

BACKGROUND OF THE INVENTION

1. Field of the Invention

The invention relates to a method and apparatus for delivering an agent into cells at a treatment site.

2. Description of the Background

Depending on the type of treatment that is being provided for a patient, systemic administration of medication can produce adverse or even toxic side effects. Local delivery can be the preferred method of treatment in that smaller total levels of medication are administered in comparison to systemic dosages, but are concentrated at a specific site. Local delivery thus produces fewer side effects and achieves more favorable results. Local delivery of medication is particularly advantageous when the treatment site is an isolated region with a biological lumen, such as a blood vessel.

Catheter-based drug delivery systems have been used to locally deliver therapeutic substances to a treatment site. Delivery catheters are generally characterized by an elongate polymeric tube having a lumen in fluid communication with a diffusion port for local delivery of therapeutic agents. One example of such a system is disclosed in U.S. Pat. No. 5,336,205 to Zenzen. Zenzen discloses an infusion catheter with an elongate tubular body having proximal and distal ends and a lumen extending between the ends through which a diagnostic, therapeutic, or vasoocclusive agent can be delivered.

Some medical conditions may require both a balloon catheter and a fluid delivery catheter to facilitate treatment. Catheter systems have been disclosed having a fluid delivery port as well as at least one inflatable balloon. For example, U.S. Pat. No. 5,415,636 to Forman teaches a dilation-drug delivery catheter including a dilation portion for dilating a stenosis and a drug delivery portion for delivering antithrombolytic, antiproliferative, or any other type of medication, to the dilation site. The drug delivery portion of the catheter is located within the dilation portion, which can be retracted to reveal the drug delivery portion after dilation.

U.S. Pat. No. 5,413,581 to Goy dislcoses a balloon dilatation catheter having a first lumen extending along the entire length of a shaft. The lumen is connected to a pump and, at the distal end of the catheter, to the inside of the balloon. The shaft has an additional lumen which opens outwards via an opening behind the proximal end of the balloon. A measuring apparatus or an apparatus for introducing a contrast medium or drug can be connected to this additional lumen.

The above-described catheter-based delivery systems bathe the diseased tissue in a composition containing the therapeutic substance or agent. Cells have a natural resistance to the passage of exogenous molecules through the cell membrane into the interior of the cells. Depending on the biological mechanism targeted, however, the therapeutic substance or agent may be most effective when acting from within the cells of the diseased tissue. Accordingly, intracellular introduction of a therapeutic substance or agent is desirable.

SUMMARY OF THE INVENTION

In accordance with one aspect of the present invention, a method of intracellular delivery of an agent is provided. The method includes positioning a catheter having a pair of needle electrodes thereon at a treatment site and causing the needle electrodes to penetrate in tissues of the treatment site. An agent is introduced through at least one of the needle electrodes to the treatment site. An electric field is applied to the treatment site by the pair of electrodes to increase permeability of the cell membranes of cells at the treatment site, wherein the agent passes through the cell membranes into the cells. In some embodiments, applying an electric field causes formation of pores in the cell membranes of the cells at the treatment site, wherein the agent passes through the pores into the cells.

In accordance with another aspect of the present invention, an intraluminal apparatus for introducing an agent into cells at a treatment site is provided. The apparatus includes a catheter assembly for accessing a treatment site through an anatomical lumen and a pair of needle electrodes carried by the catheter assembly. The pair of needle electrodes are in electrical communication with a generator for applying an electric field to the treatment site. At least one needle electrode of the needle electrode pair allows for injection of an agent to the treatment site. In some embodiments, the needle electrodes are retractable into the catheter. In other embodiments, the apparatus includes a retractable sheath that when in an extended position covers the needle electrodes and when in a retracted position exposes the needle electrodes.

BRIEF DESCRIPTION OF THE FIGURES

FIG. 2C illustrates a catheter assembly having a sheath disposed over the needle electrodes in accordance with another embodiment of the present invention;

FIG. 3 illustrates a catheter assembly having needle electrodes oriented at the distal tip thereof in accordance with another embodiment of the present invention;

FIG. 4A illustrates a catheter assembly having balloon-engagable needle electrodes in accordance with another embodiment of the present invention; and FIG. 4B illustrates the catheter assembly of FIG. 4A following engagement of the needle electrodes via inflation of the balloon.

DETAILED DESCRIPTION

The present invention provides a method and apparatus for electropermeabilization-mediated delivery of an agent into cells at a treatment site. "Electroperneabilization" refers broadly to the phenomenon wherein a cellular membrane is exposed to high-intensity electric field pulses, resulting in increased permeability of the membrane, for example through pores, to exogenous molecules.

"Electroporation" refers more specifically to the phenomenon of increased permeability following the application of electric field pulses to create physical pores in a cellular membrane, thereby allowing exogenous molecules to enter the cell though the pores in the membrane. "Cellular membrane" or "cell membrane" is defined as the membrane that bounds each cell. The cell membrane functions as a selective barrier that regulates the chemical composition of the cell by allowing some substances, such as oxygen, nutrients, and cellular waste products, to pass readily between the cell and the external environment, while impeding the entrance and exit of other substances.

Some of the various embodiments of the present invention are illustrated by FIGS. 1A–4B. The Figures have not been drawn to scale, and the size of the various structures and regions have been over or under emphasized for illustrative purposes.

Method of Introducing an Agent into Cells at a Treatment Site

The method described herein is a transluminal, catheter-based method of introducing an agent into cells at a treatment site. Accordingly, the treatment site may be any region of, on, or within an anatomical lumen, whether a part of the lumen itself, such as the vessel wall, or an extraneous structure on or within the lumen, such as an atherosclerotic or a restenotic lesion. Alternatively, the treatment site may be an anatomical region to which intraluminal access is possible, such as a chamber of the heart. "Anatomical lumen" refers to any lumen within a patient including, but not limited to, blood vessels such as arteries and veins, and other vessels or ducts, such as those of mammalian cardiovascular, lymphatic, respiratory, digestive, urinary, and reproductive systems. "Intraluminal access" refers to access through an anatomical lumen.

Figure 1A:
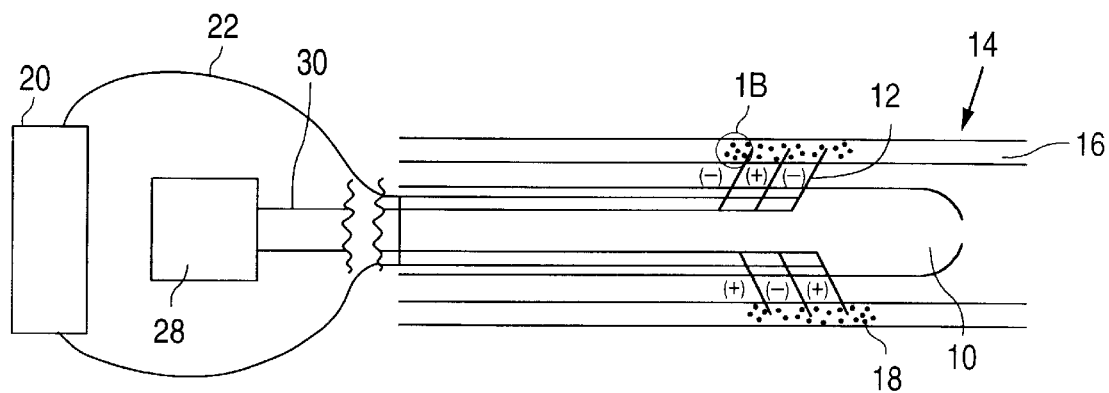
FIG. 1A illustrates a catheter assembly following the electropermeabilization-mediated release of an agent through the needle electrodes into the vessel wall.
Figure 1B:
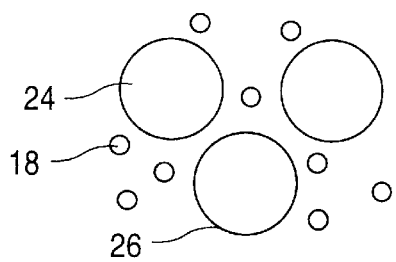
FIG. 1B is an enlarged view of the region 1B of FIG. 1A, illustrating the delivered agent surrounding the cells of the vessel wall.
Figure 1C:
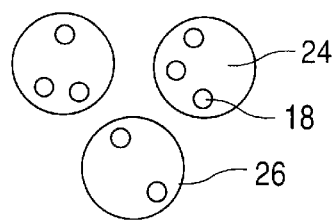
FIG. 1C illustrates the cells of FIG. 1B into which an agent has entered following electropermeabilization of the cell membranes.

Referring now to FIGS. 1A–1C, a method of introducing an agent into cells at a treatment site of a patient is illustrated. In accordance with one embodiment, a catheter assembly 10 having at least one pair of needle electrodes 12 is positioned within a vessel 14. Needle electrodes 12 at least partially penetrate a wall 16 of vessel 14. An agent, as illustrated by dotted regions 18, is delivered from a reservoir 20 via supply lumens 22 and released from at least one of the needle electrodes 12 into wall 16. Wall 16 is made up of cells 24, each of which is bounded by a cell membrane 26, as depicted in FIG. 1B. Cell membranes 26 may not be permeable to certain exogenous molecules or agents for many reasons including, but not limited to, the size of the molecule or agent, an insufficient diffusion gradient, an insufficient rate of diffusion, and the inability to find a carrier for active transport across cell membrane 26. Yet, when pulses of electricity are applied to wall 16 through needle electrodes 12, which are in electrical communication with a signal generator 28 via leads 30, cell membranes 26 are temporarily permeabilized such that an agent may enter cells 24, as shown in FIG. 1C. In some embodiments, physical pores are formed in portions of cell membranes 26 through which an agent may pass into cells 24. An agent may be released from the at least one needle electrode 12 prior to, simultaneously with, or subsequent to the application of electrical pulses. The acts, however, should be performed substantially contemporaneously for optimum uptake of an agent into cells 24.

An agent may be a drug or therapeutic substance. As used herein, the terms "drug" and "therapeutic substance" refer to any substance capable of exerting a therapeutic or prophylactic effect in the practice of the present invention. Examples of such agents include antiproliferative, antineoplastic, antiinflammatory, antiplatelet, anticoagulant, antifibrin, antithrombin, antimitotic, antibiotic, and antioxidant substances as well as combinations thereof. A suitable example of an antiproliferative substance is actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. Examples of suitable antineoplastics include paclitaxel and docetaxel. An example of an antiinflammatory substance is dexamethasone, a corticosteroid. Examples of suitable antiplatelets, anticoagulants, antifibrins, and antithrombins include sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen), and 7E-3B® (an antiplatelet drug from Centocore). Examples of suitable antimitotic agents include methotrexate, azathioprine, vincristine, vinblastine, fluorouracil, adriamycin, and mutamycin. Examples of suitable cytostatic or antiproliferative agents include angiopeptin (a somatostatin analog from Ibsen), angiotensin converting enzyme inhibitors such as CAPTOPRIL (available from Squibb), CILAZAPRIL (available from Hoffman-LaRoche), or LISINOPRIL (available from Merck); calcium channel blockers (such as Nifedipine), colchicine, fibroblast growth factor (FGF) antagonists, fish oil (omega 3-fatty acid), histamine antagonist, LOVASTATIN (an inhibitor of HMG-CoA reductase, a cholesterol lowering drug from Merck), monoclonal antibodies (such as PDGF receptors), nitroprusside, phosphodiesterase inhibitors, prostaglandin inhibitor (available form Glazo), Seramin (a PDGF antagonist), serotonin blockers, steroids, thioprotease inhibitors, triazolopyrimidine (a PDGF antagonist), and nitric oxide. One of ordinary skill in the art will appreciate that any of the exemplary substances listed above may belong to more than one of the above-noted categories and that the lists are provided by example and not limitation. Other therapeutic substances or drugs which may be appropriate include alpha-interferon, genetically engineered epithelial cells, extracellular matrix modulators, apoptosis inducers, anti-angiogenesis agents, matrix metalloproteinases (MMPs), and reperfusion injury inhibitors as well as combinations thereof.

In addition to drugs or therapeutic substances, an agent may also be a compound useful for gene therapy. Such compounds include nucleic acids (e.g., polynucleotides), peptides and polypeptides, including antibodies. Polynucleotides encode metabolic enzymes and proteins. The term "polynucleotides" includes DNA, cDNA, and RNA sequences, such as plasmids, viral vectors, antisense nucleic acids, ribozymes, and triplex substances. The term "antibodies" includes intact molecules as well as fragments thereof.

An agent may be released in a biocompatible carrier, such as saline. The dosage or concentration of an agent required to produce a favorable therapeutic effect should be less than the level at which an agent produces toxic effects and greater than the level at which non-therapeutic results are obtained. The dosage or concentration of an agent required to inhibit particular cellular activity in a vascular region, for example, can depend upon factors such as the particular circumstances of the patient; the nature of the trauma; the nature of the therapy desired; the time over which an agent resides at the vascular site; and if other bioactive substances are employed, the nature and type of the substance or combination of substances.

The same needle electrodes 12 that deliver an agent can also deliver an electric field to the treatment site. Briefly, a suitable signal generator 28, which is known to one of ordinary skill in the art, can be used to generate an electric signal for the application of an electric field of a predetermined amplitude. The electric field causes the cell membranes 26 of cells 24 at the treatment site to become sufficiently permeable to allow an agent to cross cell membranes 26 and enter cells 24.

The field strength of the electric field to be generated is determined by the nature, size, and location of the treatment site. Excessive field strength may result in lysing of cells 24 in the treatment site when cell lysis is not desired, whereas a low field strength may result in reduced efficacy of electropermeabilization and thus reduced cellular uptake of an agent.

The waveform of the electrical signal provided by pulse generator 28 can be an exponentially decaying pulse, a square pulse, a unipolar oscillating pulse train, a bipolar oscillating pulse train, or a combination thereof. The nominal electric field strength can be from about 10 V/cm to about 20 kV/cm. The nominal electric field strength is determined by computing the voltage between needle electrodes 12 in an electrode pair and dividing by the distance between the needle electrodes 12. The pulse length can be from about 10 microseconds to about 100 milliseconds. There can be any desired number of pulses, typically 1 to 100 pulses per second. The lag time between pulse sets can be any desired time, such as one second. The waveform, electric field strength, and pulse duration may also depend upon the type of cells at the treatment site and the type of agent that is to enter cells via electropermeabilization. The various parameters including electric field strengths required for the electropermeabilization of many known cell types are available to one of ordinary skill in the art.

Apparatus for Electropermeabilization-Mediated Delivery of an Agent

Catheter assembly 10 may be of any design suitable for electropermeabilization-mediated delivery of an agent into cells 24 at an intraluminally-accessible treatment site, as described herein. Catheter assembly 10 may include one or more inflatable balloons depending, in part, on the application for which catheter assembly 10 will be employed. Exemplary catheter designs for use with the disclosed method are presented herein. However, one of ordinary skill in the art will recognize that other catheter devices can be modified according to the present invention.

Referring to FIG. 1A, catheter assembly 10 includes at least one pair of opposing needle electrodes 12. Needle electrodes 12 serve as electrodes through which electrical pulses are applied. Thus, needle electrodes 12 must be made from a suitably conductive material such as, but not limited to, gold, platinum, or titanium. The particular material selected should exhibit acceptable tissue-material interactions since needle electrodes 12 contact healthy and/or diseased tissues at treatment site 14.

At least one needle electrode 12 can also serve as a conduit through which an agent may be delivered. The penetrating length of electrode needles 12 may be of any desired length suitable to deliver an agent into any targeted space. For example, the depth of penetration can range from the intima to the adventitia layers of the vascular wall. The penetrating length of electrode needles 12 may be, for example, from approximately 100 μm to approximately 700 μm. The shape of needle electrodes 12 may be of any suitable shape, so long as the selected shape does not adversely affect the delivery of electrical pulses as well as of an agent.

The distance between individual needle electrodes 12 in an electrode pair is typically fixed, but may also be adjustable. In one embodiment, each adjacent pair of electrode needles 12 should have opposite polarity. In another embodiment, wherein a plurality of arrays of needle electrodes 12 are provided about the circumference of catheter assembly 10, each array of needle electrodes 12 should be arranged such that the polarity of each needle electrode 12 is opposite that of its neighboring needle electrode 12. The neighboring array of needle electrodes 12 that is adjacent to any other array of needle electrodes 12 should be arranged such that no two needle electrodes 12 positioned adjacent to one another have the same polarity. This arrangement allows for an electric field to be distributed evenly throughout the targeted region. The treatment zone and electrical field distribution form a cylindrical surface when such arrays of needle electrodes 12 are placed longitudinally along catheter assembly 10.

Needle electrodes 12 may be oriented in any configuration on or about catheter assembly 10, such as, for example, a linear configuration along one or more regions of catheter assembly 10, a circular configuration about the circumference of catheter assembly 10, or a clustered configuration within a localized region of catheter assembly 10. The particular configuration of needle electrodes 12 depends, at least in part, on the location and characteristics of the treatment site.

Needle electrodes 12 may be oriented in any direction and at any angle relative to catheter assembly 10 so long as needle electrodes 12 are capable of being positioned to at least partially penetrate targeted tissues at the treatment site. For example, needle electrodes 12 may protrude from catheter assembly 10 essentially perpendicularly to the body of catheter assembly 10 or essentially parallel with the body of catheter assembly 10. Needle electrodes 12 may also protrude from catheter assembly 10 at an angle, for example the tips of needle electrodes 12 pointing toward the distal end of catheter assembly 10. To prevent needle electrodes 12 from causing luminal irritation or injury during intraluminal delivery, positioning, and withdrawal of catheter assembly 10, needle electrodes 12 can be retractable into the body of catheter assembly 10. Retractable needle electrodes 12 in a retracted position should retract completely into the body of catheter assembly 10, thereby allowing intraluminal movement of catheter assembly 10 to be accomplished without dragging needle electrodes 12 along the lumen wall.

Figure 2A:
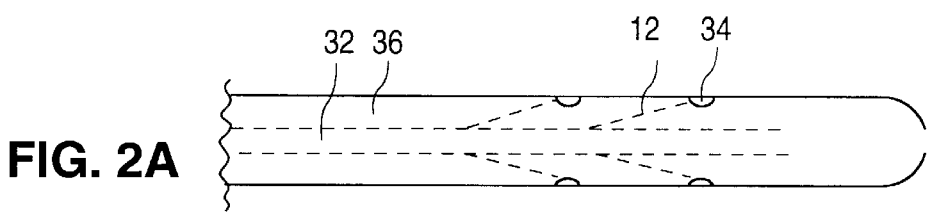
FIG. 2A illustrates a catheter assembly having retractable needle electrodes in a retracted position in accordance with one embodiment of the present invention.
Figure 2B:
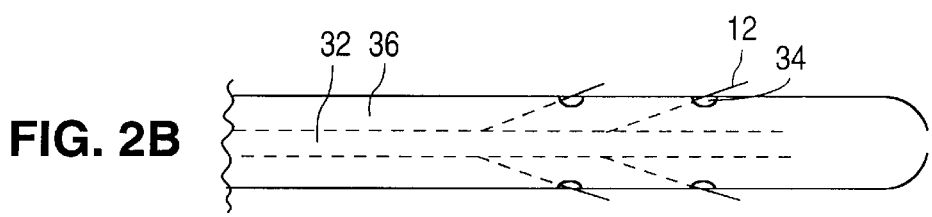
FIG. 2B illustrates the catheter assembly of FIG. 2A having retractable needle electrodes in an extended position.

FIGS. 2A and 2B illustrate needle electrodes 12 that are mounted on an inner member 32 and are retractable into the interior of catheter assembly 10 through openings 34 in an outer member 36. In operation, catheter assembly 10 may be initially positioned at a treatment site with needle electrodes 12 in a retracted position, as depicted in FIG. 2A. Once catheter assembly 10 has been successfully positioned at the treatment site, needle electrodes 12 may be extended out from catheter assembly 10 through openings 34, as depicted in FIG. 2B, to at least partially penetrate the tissues. Following electropermeabilization-mediated delivery of an agent, needle electrodes 12 may again be retracted into the interior of catheter assembly 10 through openings 34, thereby facilitating removal of catheter assembly 10 without causing luminal irritation or injury. Needle electrodes 12 may be extended and retracted by, for example, sliding inner member 32 to which needle electrodes 12 are attached forward and back, respectively, within outer member 36.

Alternatively, a retractable outer sheath may be disposed over needle electrodes 12 during intraluminal movement of catheter assembly 10 to prevent luminal irritation and injury. A sheath may be of any suitable material, size and shape for use with the method described herein. FIG. 2C illustrates a retractable sheath 38 in an extended position. Sheath 38 can be retracted to expose needle electrodes 12 such that needle electrodes 12 may at least partially penetrate tissues at the treatment site during electropermeabilization-mediated delivery of an agent. Needle electrodes 12 in this embodiment may be made of a shape memory material, such as nitinol, such that when sheath 38 is retracted, the penetrating ends of needle electrodes 12 lift off the surface of the delivery catheter and orient towards the vessel wall for penetration. Needle electrodes 12 can be securely engaged into a vessel wall 16 by a slight push on the catheter in the proximal to distal direction.

FIG. 3 illustrates an embodiment in which needle electrodes 12 are located at a distal tip 40 of catheter assembly 10. Such a configuration may be employed with retractable needle electrodes 12 and/or retractable sheath 38, as described above. This configuration of needle electrodes 12 is particularly suitable for use when the treatment site is not a tubular lumen such as vessel 14, but rather an anatomical region to which intraluminal access is possible. By example and not limitation, this embodiment of catheter assembly 10 may be useful when the treatment site is the surface of endocardium within the left ventricle of a mammalian heart. Catheter assembly 10 may access the left ventricle through the aorta and the aortic valve. Upon entering the left ventricle, retractable needle electrodes 12 may be extended, or alternatively needle electrodes 12 may be exposed by retracting overlying sheath 38, to treat discrete patches of endocardium or myocardium. In humans, the wall of the left ventricle has a thickness of about 8–9 mm. The wall of the right ventricle has a thickness of about 3–4 mm. The walls of the atria have thicknesses of about 2 mm. Accordingly, the penetrating length of electrode needles 12 may be of any appropriate length to treat the targeted endocardial or myocardial region.

In yet another embodiment, catheter assembly 10 can include an inflatable balloon. An inflatable balloon may be used for dilation of the lumen. Additionally, a balloon can be used to control the engagement and disengagement of needle electrodes 12. FIGS. 4A and 4B illustrate one such embodiment. In FIG. 4A, needle electrodes 12 are mounted on catheter assembly 10 to rest in a low-profile position against the proximal end of a balloon 42. When balloon 42 is inflated, as shown in FIG. 4B, needle electrodes 12 are extended out from catheter assembly 10. Needle electrodes 12 can be securely engaged into a vessel wall 16 by a slight push on the catheter in the proximal to distal direction. The depth of penetration of needle electrodes 12 may be controlled by the inflation pressure of balloon 42 and the size of needle electrodes 12. The needle electrodes 12 may be disengaged by deflating balloon 42 while pulling catheter assembly 10 back in the proximal direction.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of delivery of an agent, comprising:
    positioning a catheter having a pair of needle electrodes into a body lumen;
    extending said needle electrodes out from said catheter causing said needle electrodes to penetrate into the tissue surrounding said body lumen;
    introducing an agent through at least one of said needle electrodes to said tissue; and
    applying an electric field to said tissue by said pair of needle electrodes.

2. The method of claim 1, wherein said applying an electric field causes formation of pores in the cell membranes of the cells of said tissue, wherein said agent passes through said pores into the cells.

3. The method of claim 1, wherein said introducing an agent and said applying an electric field are performed substantially contemporaneously.

4. The method of claim 1, wherein said body lumen is a blood vessel.

5. The method of claim 1, wherein said agent is selected from a group of antiproliferative, antineoplastic, antiinflammatory, antiplatelet, anticoagulant, antifibrin, antithrombin, antimitotic, antibiotic, and antioxidant substances and combinations thereof.

6. An apparatus for introducing an agent to a treatment site, comprising:
    a catheter assembly for accessing a treatment site through an anatomical lumen; and
    a pair of needle electrodes integrated with said catheter assembly, said needle electrodes capable of being extended out from said catheter assembly to penetrate into tissue of said treatment site;
    wherein said pair of needle electrodes are capable of being in electrical communication with a generator for applying an electric field to said tissue of said treatment site, and wherein at least one needle electrode of said pair of needle electrodes allows for injection of an agent to said tissue of said treatment site.

7. The apparatus of claim 6, wherein one of said pair of needle electrodes is configured to receive a first charge and the other of said pair of needle electrodes is configured to receive a second charge different from said first charge.

8. The apparatus of claim 6, wherein said electric field increases the permeability of the cell membranes of cells at said treatment site.

9. The apparatus of claim 6, wherein said catheter assembly comprises at least one inflatable balloon.

10. The apparatus of claim 6, wherein said needle electrodes are located at a distal tip of said catheter assembly.

11. A method of intracellular delivery of an agent, comprising:
    positioning a catheter having a pair of needle electrodes thereon at a treatment site;
    causing said needle electrodes to penetrate in tissues of said treatment site;
    introducing an agent through at least one of said needle electrodes to said treatment site; and
    applying an electric field to said treatment site by said pair of needle electrodes to increase permeability of the cell membranes of the cells at said treatment site to allow said agent to pass through the cell membranes into the cells, wherein said electric field is a pulsed field of between 1 and approximately 100 pulses per second.

12. The method of claim 4, wherein said pulses are of a duration of between approximately 10 microseconds to approximately 100 milliseconds per pulse.

13. A method of intracellular delivery of an agent, comprising:
positioning a catheter having a pair of needle electrodes thereon at a treatment site;
causing said needle electrodes to penetrate in tissues of said treatment site;
introducing an agent through at least one of said needle electrodes to said treatment site; and
applying an electric field to said treatment site by said pair of needle electrodes to increase permeability of the cell membranes of the cells at said treatment site to allow said agent to pass through the cell membranes into the cells, wherein said electric field has a field strength of between approximately 10 V/cm and approximately 20 KV/cm.

14. A method of intracellular delivery of an agent, comprising:
positioning a catheter having a pair of needle electrodes thereon at a treatment site;
causing said needle electrodes to penetrate in tissues of said treatment site;
introducing an agent through at least one of said needle electrodes to said treatment site; and
applying an electric field to said treatment site by said pair of needle electrodes to increase permeability of the cell membranes of the cells at said treatment site to allow said agent to pass through the cell membranes into the cells, wherein said treatment site is an atherosclerotic lesion in a blood vessel.

15. A method of intracellular delivery of an agent, comprising:
positioning a catheter having a pair of needle electrodes thereon at a treatment site;
causing said needle electrodes to penetrate in tissues of said treatment site;
introducing an agent through at least one of said needle electrodes to said treatment site; and
applying an electric field to said treatment site by said pair of needle electrodes to increase permeability of the cell membranes of the cells at said treatment site to allow said agent to pass through the cell membranes into the cells, wherein the said treatment site is a restenotic lesion in a blood vessel.

16. A method of intracellular delivery of an agent, comprising:
positioning a catheter having a pair of needle electrodes thereon at a treatment site;
causing said needle electrodes to penetrate in tissues of said treatment site;
introducing an agent through at least one of said needle electrodes to said treatment site; and
applying an electric field to said treatment site by said pair of needle electrodes to increase permeability of the cell membranes of the cells at said treatment site to allow said agent to pass through the cell membranes into the cells, wherein the cells are smooth muscle cells.

17. A method of intracellular delivery of an agent, comprising:
positioning a catheter having a pair of needle electrodes thereon at a treatment site;
causing said needle electrodes to penetrate in tissues of said treatment site;
introducing an agent through at least one of said needle electrodes to said treatment site; and
applying an electric field to said treatment site by said pair of needle electrodes to increase permeability of the cell membranes of the cells at said treatment site to allow said agent to pass through the cell membranes into the cells, wherein said agent is selected from a group of extracellular matrix modulators, apoptosis inducers, anti-angiogenesis agents, matrix metalloproteinases (MMPs), and reperfusion injury inhibitors and combinations thereof.

18. A method of intracellular delivery of an agent, comprising:
positioning a catheter having a pair of needle electrodes thereon at a treatment site;
causing said needle electrodes to penetrate in tissues of said treatment site;
introducing an agent through at least one of said needle electrodes to said treatment site; and
applying an electric field to said treatment site by said pair of needle electrodes to increase permeability of the cell membranes of the cells at said treatment site to allow said agent to pass through the cell membranes into the cells, wherein said agent is selected from a group of nucleic acids, peptides and polypeptides.

19. An intraluminal apparatus for introducing an agent to a treatment site, comprising:
a catheter assembly for accessing a treatment site through an anatomical lumen; and
a pair of needle electrodes integrated with said catheter assembly;
wherein said pair of needle electrodes are capable of being in electrical communication with a generator for applying an electric field to said treatment site, and wherein at least one needle electrode of said pair of needle electrodes allows for injection of an agent to said treatment site, and wherein said electric field has a field strength of between approximately 10 V/cm and approximately 20 KV/cm.

20. An intraluminal apparatus for introducing an agent to a treatment site, comprising:
a catheter assembly for accessing a treatment site through an anatomical lumen; and
a pair of needle electrodes integrated with said catheter assembly;
wherein said pair of needle electrodes are capable of being in electrical communication with a generator for applying an electric field to said treatment site, and wherein at least one needle electrode of said pair of needle electrodes allows for injection of an agent to said treatment site, and wherein said apparatus is used for intracellular delivery of an agent to an atherosclerotic region of a blood vessel.

21. An intraluminal apparatus for introducing an agent to a treatment site, comprising:
a catheter assembly for accessing a treatment site through an anatomical lumen; and
a pair of needle electrodes integrated with said catheter assembly;
wherein said pair of needle electrodes are capable of being in electrical communication with a generator for applying an electric field to said treatment site, and wherein at least one needle electrode of said pair of needle electrodes allows for injection of an agent to said treatment site, and wherein said apparatus is used for intracellular delivery of an agent to a restenotic region of a blood vessel.

22. An intraluminal apparatus for introducing an agent to a treatment site, comprising:
   a catheter assembly for accessing a treatment site through an anatomical lumen; and
   a pair of needle electrodes integrated with said catheter assembly;
   wherein said pair of needle electrodes are capable of being in electrical communication with a generator for applying an electric field to said treatment site, and wherein at least one needle electrode of said pair of needle electrodes allows for injection of an agent to said treatment site, and wherein said apparatus is used for intracellular delivery of an agent to a region of a mammalian heart.

23. An intraluminal apparatus for introducing an agent to a treatment site, comprising:
   a catheter assembly for accessing a treatment site through an anatomical lumen; and
   a pair of needle electrodes integrated with said catheter assembly;
   wherein said pair of needle electrodes are capable of being in electrical communication with a generator for applying an electric field to said treatment site, and wherein at least one needle electrode of said pair of needle electrodes allows for injection of an agent to said treatment site, and wherein said needle electrodes are retractable into said catheter.

24. An intraluminal apparatus for introducing an agent to a treatment site, comprising:
   a catheter assembly for accessing a treatment site through an anatomical lumen;
   a pair of needle electrodes integrated with said catheter assembly, wherein said pair of needle electrodes are capable of being in electrical communication with a generator for applying an electric field to said treatment site, and wherein at least one needle electrode of said pair of needle electrodes allows for injection of an agent to said treatment site; and
   a retractable sheath having an extended position and a retracted position, wherein when in said extended position said sheath covers said needle electrodes and when in said retracted position said needle electrodes are exposed.

25. An intraluminal apparatus for introducing an agent to a treatment site, comprising:
   a catheter assembly for accessing a treatment site through an anatomical lumen; and
   a plurality of needle electrodes integrated with said catheter assembly, said needle electrodes capable of being extended out from said catheter assembly to penetrate into tissue of said treatment site;
   wherein said needle electrodes are configured to be in electrical communication with a generator for applying an electric field to said treatment site, and wherein at least one of said needle electrodes allows for injection of an agent to said treatment site, and wherein said needle electrodes are oriented about the circumference of said catheter assembly.

* * * * *

UNITED STATES PATENT AND TRADEMARK OFFICE
CERTIFICATE OF CORRECTION

PATENT NO. : 6,625,486 B2  Page 1 of 1
DATED : September 23, 2003
INVENTOR(S) : Lundkvist et al.

It is certified that error appears in the above-identified patent and that said Letters Patent is hereby corrected as shown below:

Column 1,
Line 45, change "to Goy dislcoses" to -- to Goy discloses --.

Column 2,
Line 61, change "Electroperneabilization" to -- Electropermeabilization --.

Column 3,
Line 3, change "the cell though the pores" to -- the cell through the pores --.

Signed and Sealed this

Ninth Day of December, 2003

JAMES E. ROGAN
*Director of the United States Patent and Trademark Office*